(12) United States Patent
Linnenkohl et al.

(10) Patent No.: US 8,137,738 B2
(45) Date of Patent: Mar. 20, 2012

(54) METHOD AND APPARATUS FOR RECOGNIZING A STRUCTURE TO BE APPLIED ONTO A SUBSTRATE WITH MULTIPLE CAMERAS

(75) Inventors: Jan Anders Linnenkohl, Bensheim (DE); Andreas Tomtschko, Weinsberg (DE); Mirko Berger, München (DE); Roman Raab, München (DE)

(73) Assignee: Quiss GmbH (DE)

( * ) Notice: Subject to any disclaimer, the term of this patent is extended or adjusted under 35 U.S.C. 154(b) by 1001 days.

(21) Appl. No.: 10/584,229

(22) PCT Filed: Dec. 23, 2004

(86) PCT No.: PCT/EP2004/014697
§ 371 (c)(1),
(2), (4) Date: Jun. 29, 2007

(87) PCT Pub. No.: WO2005/063407
PCT Pub. Date: Jul. 14, 2005

(65) Prior Publication Data
US 2007/0292629 A1    Dec. 20, 2007

(30) Foreign Application Priority Data

Dec. 23, 2003 (DE) .................................. 103 61 018

(51) Int. Cl.
*C23C 16/52* (2006.01)

(52) U.S. Cl. ......... 427/8; 427/207.1; 427/256; 427/284; 427/286; 427/287; 250/221

(58) Field of Classification Search .................. 250/221; 427/8
See application file for complete search history.

(56) References Cited

U.S. PATENT DOCUMENTS 6,541,757 B2 * 4/2003 Bieman et al. ............... 250/221
* cited by examiner

*Primary Examiner* — David Turocy
*Assistant Examiner* — Andrew Bowman
(74) *Attorney, Agent, or Firm* — Brooks Kushman P.C.

(57) ABSTRACT

Disclosed is a method or device for recognizing a structure, preferably a bead or trace of adhesive material (20), which is to be applied to a substrate (30), with the aid of at least two cameras, more particularly three or more cameras (12, 13, 14). The structure, which is to be applied, is applied to the substrate using an applicator device (11), whereupon the structure, which is applied to the substrate by means of the applicator device, is monitored by the cameras in such a way that the cameras are oriented towards the applied structure with at least one overlapping area, wherein the applied structure, particularly the edges of the trace of adhesive, is determined on a revolving orbit around the applicator device and the revolving orbit is pre-defined in such a way that the applied structure intersects the revolving orbit after it has been applied to the substrate.

23 Claims, 7 Drawing Sheets

METHOD AND APPARATUS FOR RECOGNIZING A STRUCTURE TO BE APPLIED ONTO A SUBSTRATE WITH MULTIPLE CAMERAS

The present application relates to and claims priority from European Application Serial No. PCT/EP2004/014697 filed Dec. 23, 2004, titled "METHOD FOR THE RECOGNITION OF A STRUCTURE WHICH IS TO BE APPLIED TO A SUBSTRATE, USING SEVERAL CAMERAS AND DEVICE THERFORE", the complete subject matter of which is hereby expressly incorporated in its entirety.

The present invention relates to a method and apparatus for recognizing a structure to be applied onto a substrate with at least two or more cameras.

For recognizing a structure to be applied onto a substrate, it has been customary to carry out optical measurements. Frequently various systems for fully automatic testing of the structure, including adhesive and sealing agent lines, are used for recognizing a structure to be applied onto a substrate. For this purpose, multiple video cameras are directed at the structure to be recognized, and, in addition, an illumination module serving to generate a contrast-rich camera image is required.

In this context, there is a need for a method for recognizing a structure to be applied onto a substrate using at least two or more cameras, while the method monitors with high accuracy and speed while an application structure or adhesive line being applied. In order to provide for error-free monitoring with multiple cameras, it is essential to carry out the image analysis of the individual cameras such that the software for evaluation of the recorded images can process this data in a suitable fashion.

Another problem in this context is the line-shaped progression of the adhesive line on the substrate because the adhesive line switches from the monitoring area of one camera to the monitoring area of another camera as a function of the motion of the application facility relative to the substrate.

An object of the present invention is to provide a method for recognizing a structure to be applied onto a substrate for at least two or more cameras. The method facilitates the monitoring of an application structure or adhesive line at high accuracy and speed, in particular during the application of the adhesive line to the substrate.

Moreover, an object of the present invention is to provide a suitable apparatus for carrying out the method according to the invention.

According to the invention, the structure to be applied is applied onto the substrate by an application facility and then the structure is monitored by the cameras such that at least an overlapping area of the cameras is directed at the applied structure. The applied structure, in particular the edges of the adhesive line, is transmitted on a surrounding track, and the surrounding track is predefined such that the applied structure intersects the surrounding track after being applied onto the substrate. The surrounding track forms a predetermined and predefined area around the application facility such that the adhesive line can be monitored independent of the travel of a robot or the application facility. Further, the surround track can be analyzed in a simple fashion by means of software. This allows the application structure or adhesive line to be monitored at a high rate while it is being applied onto the substrate, in particular if the cameras are arranged in a fixed position on the application facility.

Moreover, an advantage is if the surrounding track has a closed form around the application facility for determining the adhesive line, the adhesive line on the surrounding track on the substrate is monitored by means of a projection.

According to one embodiment, the adhesive line on the surrounding track is determined in the form of an essentially circular caliper. The circular caliper facilitates the further processing of the data recorded on the circular caliper by means of software that can be implemented and processed due to the simple geometric shape.

According to another embodiment, the adhesive line on the surrounding track is determined essentially in an elliptical form, a polygonal form, or as continuous lines.

If the center point or the center of the surrounding track essentially coincides with the site that corresponds to the site projected on the substrate by the application facility with regard to the adhesive line, then the adhesive line always reaches the surrounding track essentially with a uniform distance independent of the travel path in order to be able to monitor even a narrow radius of adhesive application for the determination.

According to an embodiment of the invention, three cameras are directed around the application facility on the surrounding track. Each camera monitors the applied structure using one overlapping area that is monitored by the neighboring camera. Consequently, at least one or two cameras can simultaneously monitor the progression of the adhesive line to be monitored in any direction.

Each camera monitors a part of the surrounding track such that the individual parts of the surrounding track monitored by each of the cameras join with the corresponding overlapping areas to form a continuous surrounding track that progresses around the application facility as the area is monitored.

According to an embodiment of the invention, each camera monitors a segment of the surrounding track essentially in the form of a circular line forming a circular caliper. In this context, the angle values of the circular line range from 0° to 360° to form a global coordinate system. The individual cameras are assigned to image one segment of the circular line with adjacent overlapping areas. This allows errors at the transition from one camera to the next camera to be reduced.

An advantage is for the angle values of the circular line that range from 0° to 360° to form a global coordinate system of the individual cameras, whereby a segment of the circular line is assigned to the images of the individual cameras. As a result, the progression of the adhesive line can be followed by at least one active camera, whereby the entire adhesive line as well as its position and/or progression can be made by relatively simple means.

According to a preferred embodiment where three cameras are used, a first camera covers a range of angles from −10° to 130°, a second camera a range of angles from 110° to 250°, and a third camera a range of angles from 230° to 10°.

Moreover, during the progression of the adhesive line, an advantage is to switch automatically from one camera to the next when the adhesive line progresses from the segment of a circular line of one camera via the overlapping area to the segment of a circular line of a different camera. As a result, it is feasible to reliably follow the predictable progression of the line and/or position of the line. Therefore, fully automatic switching between neighboring cameras can occur such that the parameterization times are reduced.

Moreover, an advantage is if the edge of the adhesive line is determined on a circular line around the application facility, the adhesive line is detected, at any progression, in a defined area. According to a preferred embodiment, the center of the circular line or of the surrounding track essentially coincides with the site from which the adhesive emanates to form the adhesive line, whereby each camera monitors at least one segment of the circle formed by the circular line.

Errors at the transition from one camera to the next can be reduced by having each camera monitor at least one overlapping area jointly with at least one adjacent camera.

The individual cameras are calibrated in order to assign an angle assignment of the individual cameras according to the circular caliper. In particular a circular arc of the calibrating facility with marker points at 0°, 120°, and 240° is used for the three cameras. This allows a global coordinate system to be used with regard to the angle assignment for the individual cameras on the circular caliper around the application facility to simplify the image processing by the software.

According to a preferred embodiment of the invention, only a strip of the camera image is processed by each camera in order to form a sequence of images from the individual strips of the camera images. The closed surrounding track is assembled from the strips of the individual camera images. By processing image strips to form a sequence of images, the image recording frequency can be increased in proportion with the data reduction achieved by recording only a strip of the image such that the speed of monitoring of the application structure can be increased.

The present invention provides an apparatus for recognizing a structure to be applied onto a substrate, preferably an adhesive line or adhesive track. At least one illumination module and one sensor unit are provided. The sensor unit includes at least two or more cameras which are provided and arranged around the facility for applying the structure, and each camera is directed at the facility for applying the structure. Furthermore, at least one overlapping area of the cameras is directed at the applied structure. The applied structure, in particular the edges of the adhesive line, is determined on a surrounding track around the application facility. In addition, the surrounding track is predefined such that the applied structure intersects the surrounding track after being applied onto the substrate. Thus, the travel path of the facility over a substrate and/or a travel path of the substrate relative to the application facility can be monitored at all times and in all directions by means of directing the cameras at the application facility by means of the surrounding track.

If the axial longitudinal axis of the individual cameras approximately intersects, in the direction of view, the axial longitudinal axis of the application facility, an advantage is that a narrow area around the application facility can be monitored at a suitable resolution and a high image recording rate.

According to a preferred embodiment, individual cameras (e.g., three cameras) are arranged at equal distances from each other in the direction of the circumference.

The individual cameras are circuited such that the images of the cameras are stored in a sequence of images such that these images can be recorded synchronously, in parallel, and in an assigned fashion.

For a higher rate of processing of the images recorded by the cameras, an advantage for each camera is to record only a strip of the image and form a part of the sequence of images.

According to a development of the invention, the cameras form a circular caliper whose center is formed by the application facility of the structure. Thus, one or more circular calipers can be used to facilitate the determination of the edge of the adhesive line on a circular line.

Another advantage consists of each camera monitoring a part of the surrounding track such that the individual parts of the surrounding track, plus the overlapping areas, form a closed surrounding track that progresses around the application facility in the form of a monitoring area on the substrate.

According to a preferred embodiment, the individual cameras comprise an overlapping area of at least 10° each relative to the next camera. This overlapping area facilitates fully automatic switching between neighboring cameras when the adhesive line progresses from the monitoring area of one camera to the next. Because the selection of the camera is not bound to the robot position or to a time component, but rather refers to the actual inspection results, i.e. is based on the arrangement on the circular line of the circular caliper and/or the global coordinate system formed thereby.

Moreover, an advantage is to use a calibrating disc with individual form elements for calibrating the individual cameras for the assignment of the angle assignment. The form elements comprise, in particular, an angle distance of essentially 10° that allows for assignment of the scaling factor, angle assignment, and center as well as a radius of the search circle for the individual cameras. In order to calibrate the three cameras, the calibrating disc comprises at least three marker sites that are arranged in a circular arc of the calibrating disc essentially at 0°, 120°, and 240°.

Advantageous developments of the invention shall be illustrated in an exemplary fashion by means of the following drawings.

Figure 1:
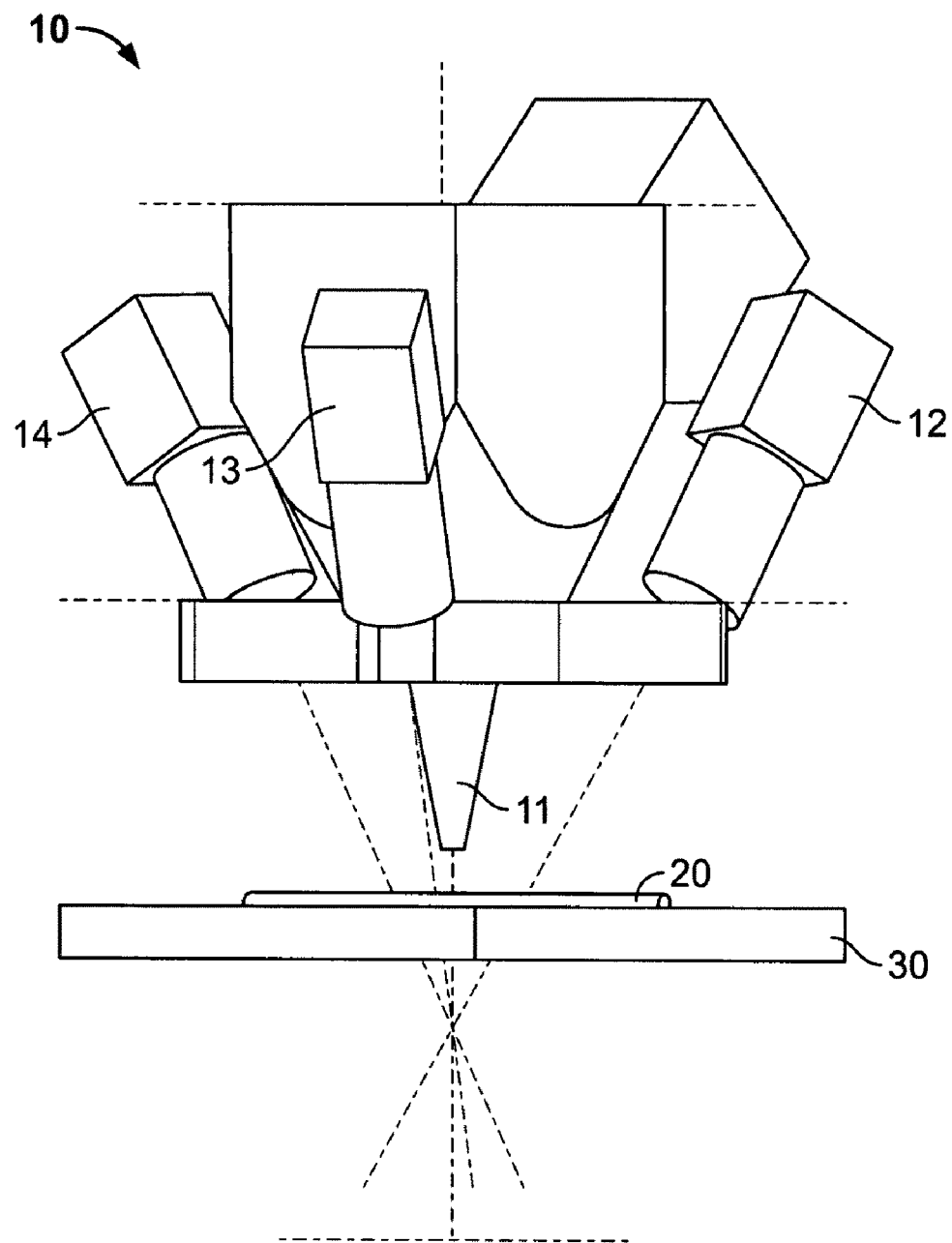
FIG. 1 illustrates a schematic side view of an apparatus for application and monitoring of an adhesive line according to an embodiment of the invention.
Figure 2:
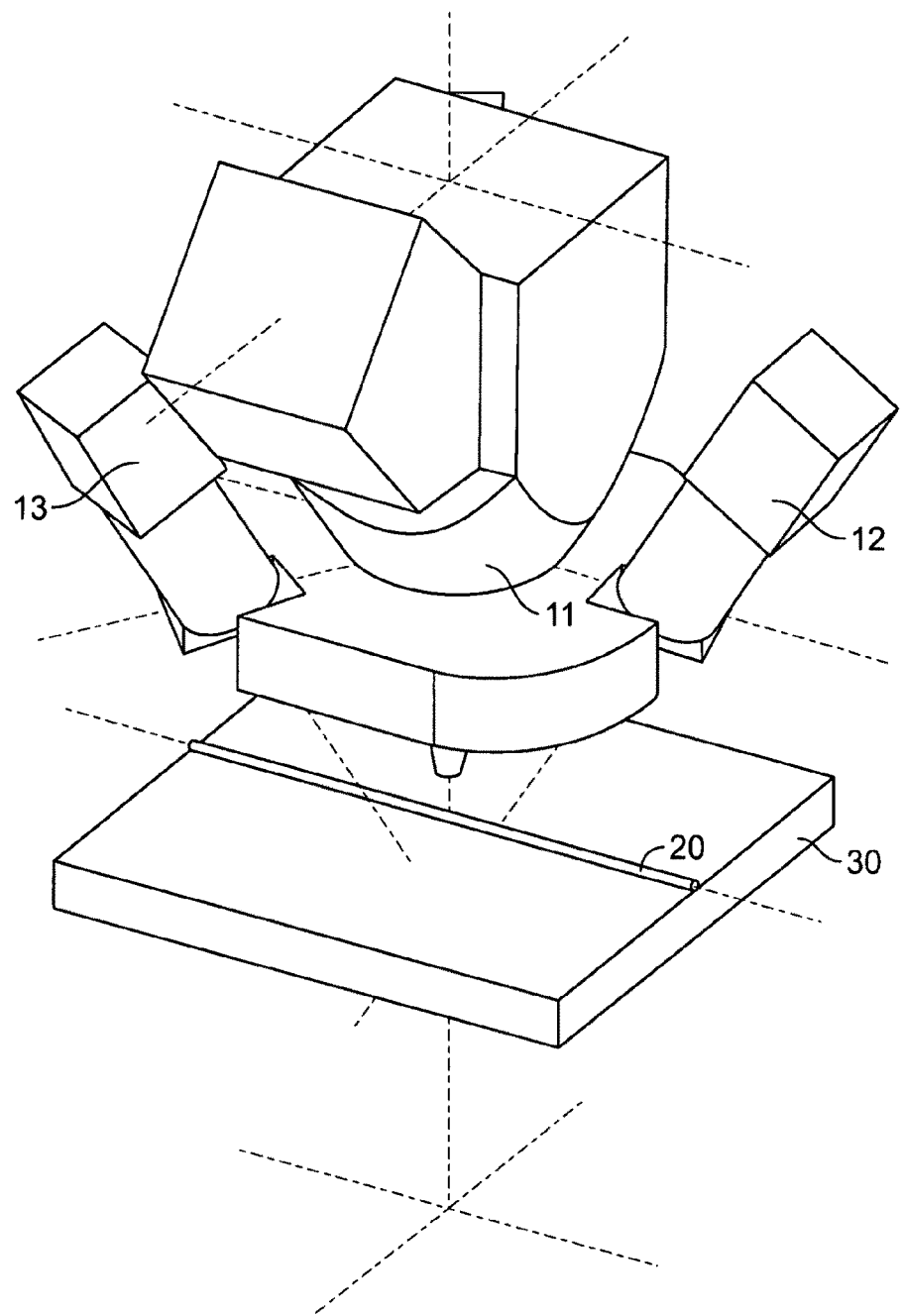
FIG. 2 illustrates a perspective view of the apparatus shown in FIG. 1 according to an embodiment of the invention.

FIGS. 1 and 2 illustrate an apparatus for recognizing a structure to be applied onto a substrate. Apparatus 10 applies and recognizes an adhesive line. In the center of the apparatus 10 according to the invention is arranged an application facility 11 by means of which an adhesive line 20 is applied onto a substrate 30 and/or onto a sheet of metal 30 proceeding from right to left (shown in FIG. 1). Three cameras 12, 13, 14 are arranged at equal distances from each other in a circle around the application facility 11, each of which is directed at the application facility 11. As is evident from FIG. 1, the axial longitudinal axes of the three cameras 12, 13, 14 intersect the axial longitudinal axis of the application facility 11 just below the substrate 30 such that the focus of the individual cameras 12, 13 and 14 is arranged right around the area of the application facility 11, in particular on a circular line.

In the inspection of the adhesive, either the application facility 11 with the cameras 12, 13, and 14 or the substrate 30 is moved, whereby the adhesive line 20 is simultaneously applied to the substrate 30 by means of the application facility 11. The cameras 12, 13, 14 monitor the applied structure. Either the application facility 11 with the cameras 12, 13 and 14 or the substrate 30 can be moved in order to apply the adhesive line onto the substrate 30 such as to follow a desired progression. By this means, the cameras 12, 13 and 14 being moved along can monitor, independent of the path of travel, as the adhesive line 20 is being applied. In FIG. 2, the adhesive line 20 progresses from left to right and is indicated by a continuous line. The intended progression of the adhesive line 20 is indicated by a dashed line to the right of the application facility 11.

Figure 3:
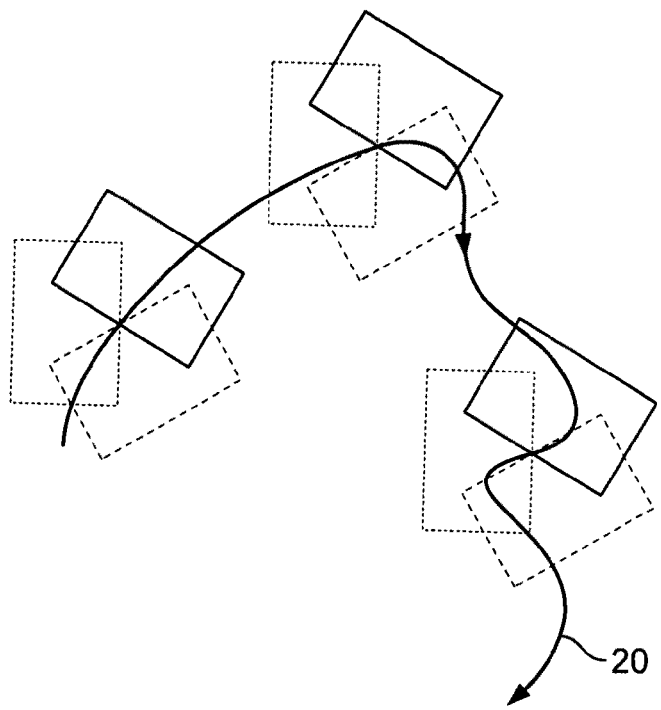
FIG. 3 illustrates the travel path of the apparatus according to the invention for application and monitoring of an adhesive line according to an embodiment of the invention.

FIG. 3 shows the progression of the adhesive line 20 as indicated by arrows, whereby the direction and/or field of view of the three individual cameras is shown in three sites. The field of view of the three individual cameras is indicated by a rectangle drawn with a continuous line, a rectangle drawn with widely dashed lines, and a rectangle drawn with narrow dashed lines. The direction of the individual fields of view of the cameras remains constant at all times whereby only the whole apparatus is moved.

Figure 4:
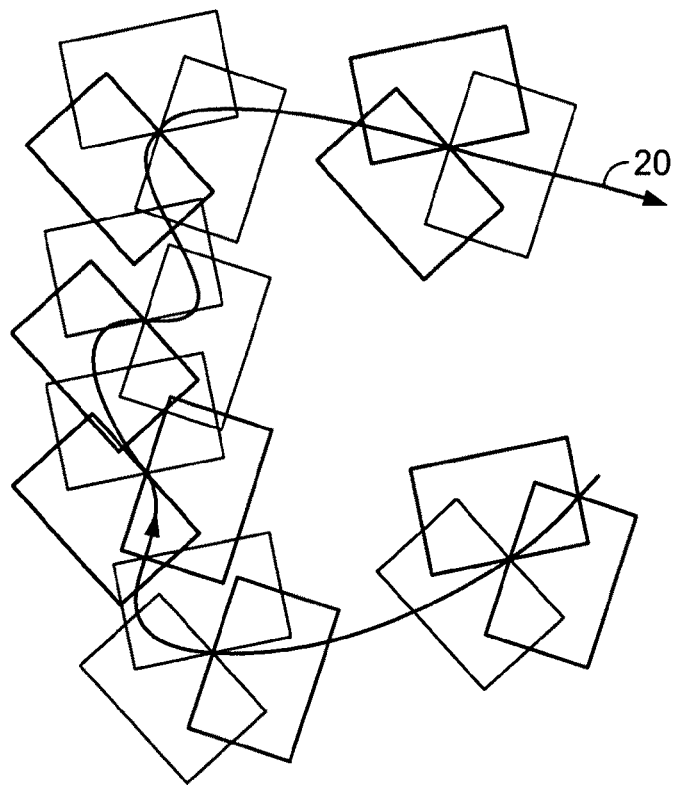
FIG. 4 illustrates another travel path of the apparatus with regard to the switching of a relevant camera according to an embodiment of the invention.

FIG. 4 shows another progression of an adhesive line 20. The field of view that is active is shown, namely which camera has the corresponding field of view is shown as a rectangle while traveling along the adhesive line. Only one camera is active at one site, and two cameras are active at another site. Which field of view is active, depends on the progression of the adhesive line relative to the circular caliper that is used to monitor the adhesive line on the substrate.

Figure 5:
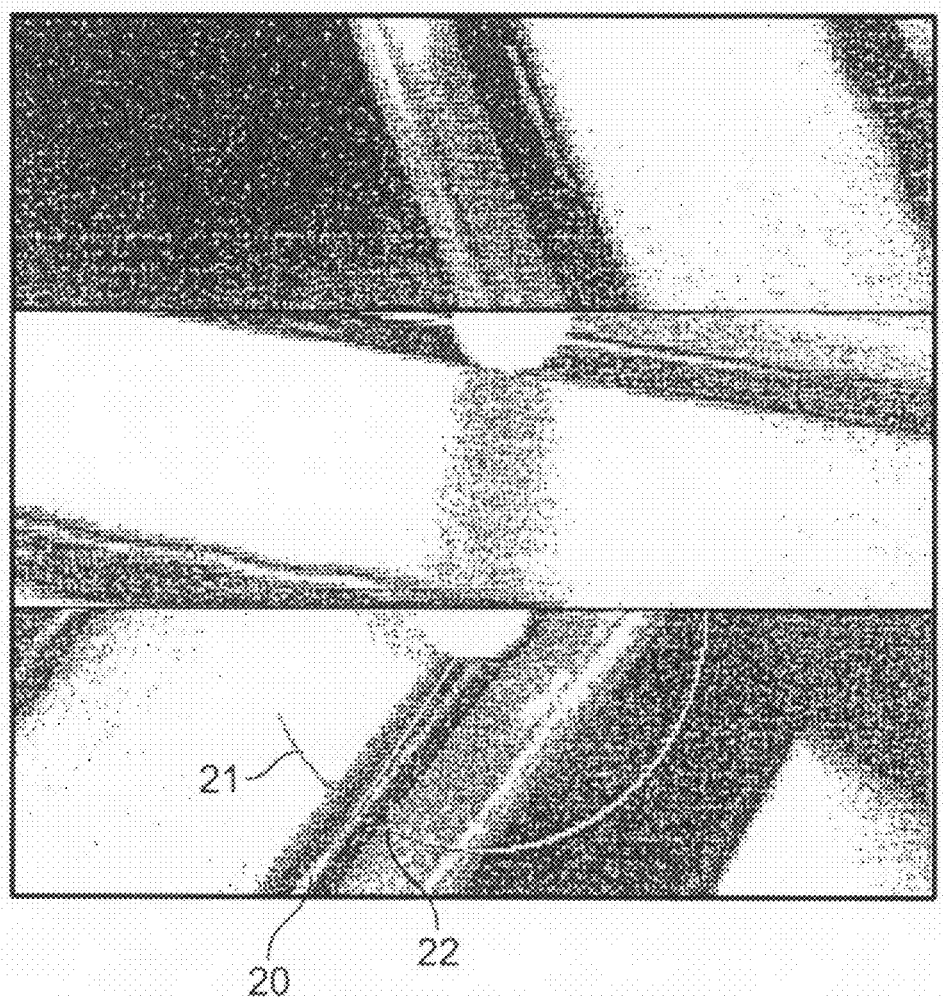
FIG. 5 illustrates a view of a single image composed of three image strips from three cameras for online monitoring according to an embodiment of the invention.

FIG. 5 shows three image strips which represent a relevant section and/or strip of an image of the three individual cameras (shown in FIG. 1). According to the method of the invention, each camera can record a strip of the image in order to reduce the amount of data such that the recording rate can be increased. These individual image strips of the three cameras are then joined into an image, whereby the image recording occurs at defined fixed time intervals and are independent of the robot control of the application facility. For example, instead of an image height of 480 pixels the cameras only record a strip of the image, where an image height of approximately. 100 pixels (e.g., 100 image lines) is used. Accordingly, by means of this partial scanning technique, (i.e., partial reading-out of the image recording chip) only small data streams are generated such that the image recording rate can be increased several-fold. In the data analysis, the images of the individual can be captured by the cameras synchronously in parallel as well as simultaneously. Then the images can be joined into a single image. The three image strips are arranged one below the other. As a result, the three images (i.e. the three image strips), are correctly arranged and assigned with regard to location and time relative to each other and can be processed accordingly. This specific image recording technique therefore facilitates simultaneous and parallel recording of individual camera images. Thus it becomes feasible to scan a structure once during the teach-in of a reference application structure, and the images of all the cameras are stored in a sequence of images.

Once the images of the three cameras are stored in a sequence of images, a parameterization of the reference track is carried out as the subsequent step of teaching-in the reference adhesive line. The robot travel path, robot travel time, direction, width, and quality of the adhesive line are used in the parameterization.

The parameterization results in a type of vector chain for the adhesive line, which allows the high image recording rate and comparably short partial sections (between 1+ and 3 mm) to be attained. Vectorization has another advantage in that the adhesive line, being in the form of a vector chain, can be stored in a camera-transcending global coordinate system.

The bottom strip of (FIG. 5) shows a caliper for gray scale value scanning arranged around the center of the application facility 11 in the form of a circular line. The two edge points 21 and 22 of the adhesive line 20 are arranged on the circular line as shown in the bottom of the Figure. The circular line is subdivided such that a range of angles from −10° to 130° is assigned to a first camera, a range of angles from 110° to 250° is assigned to a second camera, and a range of angles from 230° to 10° is assigned to a third camera. A gapless coverage is facilitated around the application facility 11 by overlapping areas of the individual cameras. From the gapless coverage a global coordinate system results for the three image strips that can be Cartesian or polar.

If the adhesive line progresses out of the field of view of a camera, the adhesive line is transiently in the overlapping area of the ranges of angles of the two cameras. If the adhesive line then progresses from the segment of the circular line of the one camera via the overlapping area to the segment of the circular line of another camera, an automatic switch is made the one camera to the other camera. This is shown in FIG. 4 by means of the active fields of view of the individual cameras.

The advantages mentioned above are attained by the individual cameras forming a circular caliper whose center is formed by the application facility 11, whereby the search for the edges 21, 22 of the adhesive line on a circular line proceeds directly around the application facility 11. For this purpose, it is essential that the individual cameras are directed at the application facility 11, whereby the axial longitudinal axes of the individual cameras intersect the longitudinal axis of the application facility 11. In particular the width of the pair of edges, of the right and the left edge of the adhesive line, the mean gray scale value of the projected gray scale value profile between the pair of edges, the edge contrast, and the progression of the position are included in the calculation by means of an assessment function in the software.

The teach-in process of the reference adhesive line can be started by the user by means of a mouse click on the line which indicates the position of the adhesive line. A mouse click on the adhesive line provides for fully automatic recognition of a position and a direction of the adhesive line in the subsequent camera images, because the image recording rate is sufficiently high and the individual images are recorded very shortly after one another, (e.g. every 1 mm to 3 mm). From the starting point, the adhesive is scanned image by image, whereby the adhesive line position and the adhesive line angle detected in the current image are used for the upcoming image as a priori knowledge. The track radii usually exceed 20 mm, which facilitates fully automatic capture of the adhesive line without a human being having to determine and/or assess the image and/or the position of the adhesive line. As a result, the search area can be limited which allows, by means of the high image recording rate, a determination of where the adhesive line will essentially progress in the following image.

Figure 6:
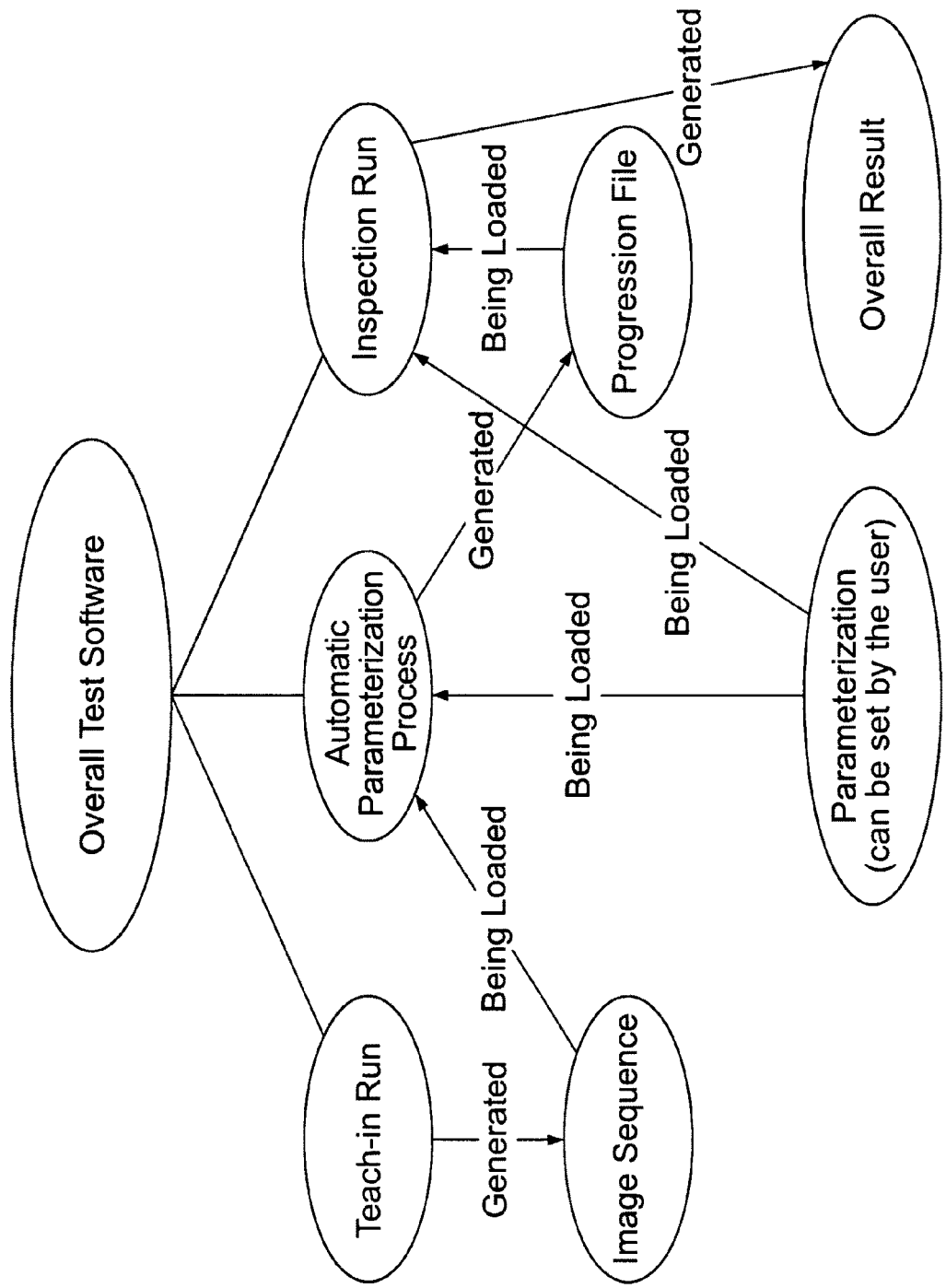
FIG. 6 illustrates the principles of the design of the software according to an embodiment of the invention.

FIG. 6 shows the principles of the design of the software, whereby the teach-in run and/or teaching-in run generates the image sequence and facilitates the automatic parameterization. The parameterization can be pre-set by the user, if applicable, and can be used jointly with a progression file for inspection of an applied adhesive line during the inspection run.

The online monitoring of an applied adhesive line is provided as follows. The application facility 11 (shown in FIG. 1) applies the adhesive line onto the metal sheet 30, whereby the application facility 11 is moved jointly with the cameras over the metal sheet 30. However, a kinematic inversion is also feasible, i.e. the metal sheet 30 being moved and the application facility with the cameras being arranged to be fixed in position. The applied adhesive line 20 is determined and analyzed synchronously and in parallel by the cameras 12, 13, 14 on the circular line of the circular caliper (shown in FIG. 5). Each camera records only a strip of the image and joins these into a single image to form a sequence of images. The image recording rate is increased in accordance with the data reduction attained by each camera recording only a strip of the image. The individual image strips in the joint image facilitate the synchronous, the parallel, as well as simultaneous capture of the three camera images. The individual images of the three cameras can be assigned directly as a function of location. As a result, online monitoring of the adhesive line in real-time is feasible, which achieves high accuracy at high travel speeds due to the high image recording rate both in teaching-in a reference adhesive line and in the inspection of the applied adhesive line. In this context, the information concerning the adhesive line in the adhesive search area, the angle assignment of the sensor, the adhesive assessment, the robot travel path, and the robot travel time are summarized in a progression list.

According to an embodiment of the present invention, an assessment function, (e.g., a fuzzy assessment), can be used to find the edges of the adhesive line. In order to determine and assess the adhesive line, the following parameters are included in the calculation of a fuzzy assessment: Width of the pair of edges (e.g., 1: left edge of the adhesive line, edge 2: right edge of the adhesive line); mean gray scale value of the projected gray scale value profile between the pair of edges; edge contrast (e.g., geometric mean of the amplitudes of the two edges); and progression of position (e.g., directed deviation of the center between the two adhesive edges from the center of the search area, in pixels). The adhesive line can be recognized automatically and described very accurately and reliably by means of the plurality of parameters, and the use of the fuzzy assessment function.

An illumination module (not shown here) for the apparatus according to the invention includes light emitting diodes (LEDs), such as infrared LEDs, ultra-violet (UV) LEDs or red-green-blue (RGB) LEDs. In order to attain high contrast in image recording, the LEDs can be flashed, (i.e. short, strong pulses of current on the order of 1.0 to 0.01 ms can be applied to the diodes). Thus, the light-emitting diodes are capable of emitting light of various colors, such that the sensor design can be switched to other types of adhesive and/or colors of adhesives without reconfiguration.

Figure 7:
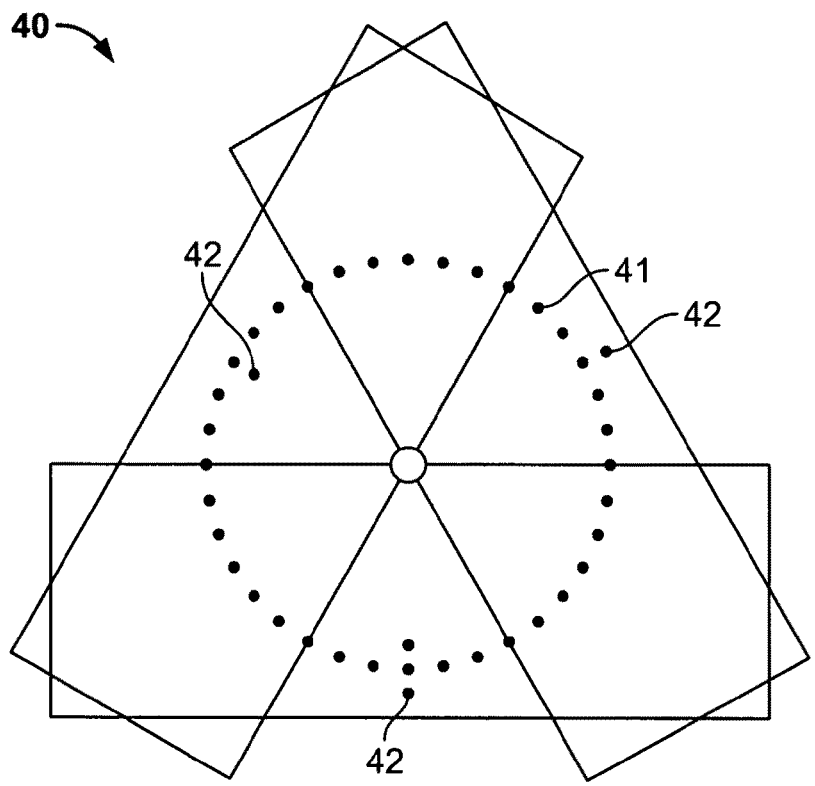
FIG. 7 illustrates a schematic view of a calibrating device for calibrating the individual cameras of the apparatus according to the invention for recognizing a structure to be applied onto a substrate according to an embodiment of the invention.

FIG. 7 shows a calibration facility 40 in the form of a circular calibrating disc in order to assign to the individual cameras their scaling factor, their angle assignment, and the center as well as the radius of the search circle. The calibrating disc consists of individual form elements and/or dots 41 that are arranged on a circular line and at an angle distance of approximately 10°. Moreover, marker sites 42 are arranged at equal distance from each other in order to calibrate the three cameras. A compensation calculation is used to calculate from the coordinates of the centers of the individual dots, the scaling factors of the individual cameras and, the center as well as radius of the search area. The marker sites at angles of 0°, 120°, 240° in the global coordinate system allow the angle assignment and the corresponding fields of view of the individual cameras to be determined. The field of view of the individual cameras is indicated, in particular, by the three rectangles in FIG. 7, whereby the form elements 41 can correspond to the circular line of the circular caliper for detection of the adhesive line.

According to an embodiment that is not shown, multiple circular calipers are formed by multiple cameras that are arranged around the application facility, but are attached at different radii from the center of the application facility. For inspection of an application structure and/or adhesive line, the cameras are directed at a circle and/or circular line whose center coincides with the center of the application facility. The optical detection of the adhesive line proceeds on this circular line.

Figure 8:
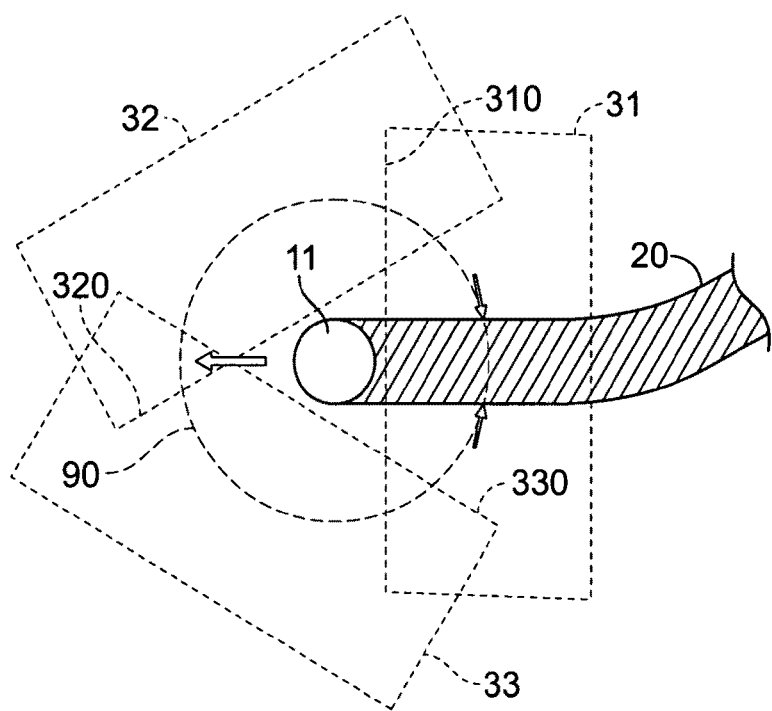
FIG. 8 illustrates a schematic view of the adhesive line with the circular caliper and the image strip of the individual cameras according to an embodiment of the invention.

FIG. 8 shows the adhesive line 20 applied onto the substrate by the nozzle of the application facility 11. The circular caliper 90, provided by the individual cameras to be concentric around the application facility 11, is used in the analysis of the applied adhesive line 20. The dashed rectangles correspond to the image strip of the individual cameras is used by the software for analysis. The rectangle 31 is assigned to the first camera as image strip, the rectangle 32 is assigned to the second camera as image strip, and the rectangle 33 is assigned to the third camera as image strip, The individual image strips of the individual cameras each comprise an overlapping area with respect to the neighboring camera. The gray scale value scanning of the circular caliper 90 is carried out by the rectangle 31 of the first camera (shown in FIG. 8), whereby the edges shown by the small arrows are used for assessment of the quality of the adhesive line (as shown in FIG. 5). Accordingly, only the first camera is active according to image strip 31 (shown in FIG. 8), as illustrated above according to FIGS. 3 and 4. The circular caliper also extends into the overlapping area of the individual image strips 31, 32, 33 such that the two neighboring cameras become active in the circle segment of the circular caliper 90. The circle segment resides in the overlapping area of 2 image strips 31, 32, and 33, when the adhesive line 20 in this area is shifted and/or progresses due to a track-shaped and/or curved progression (as shown schematically by the large arrow in FIG. 8).

Figure 9:
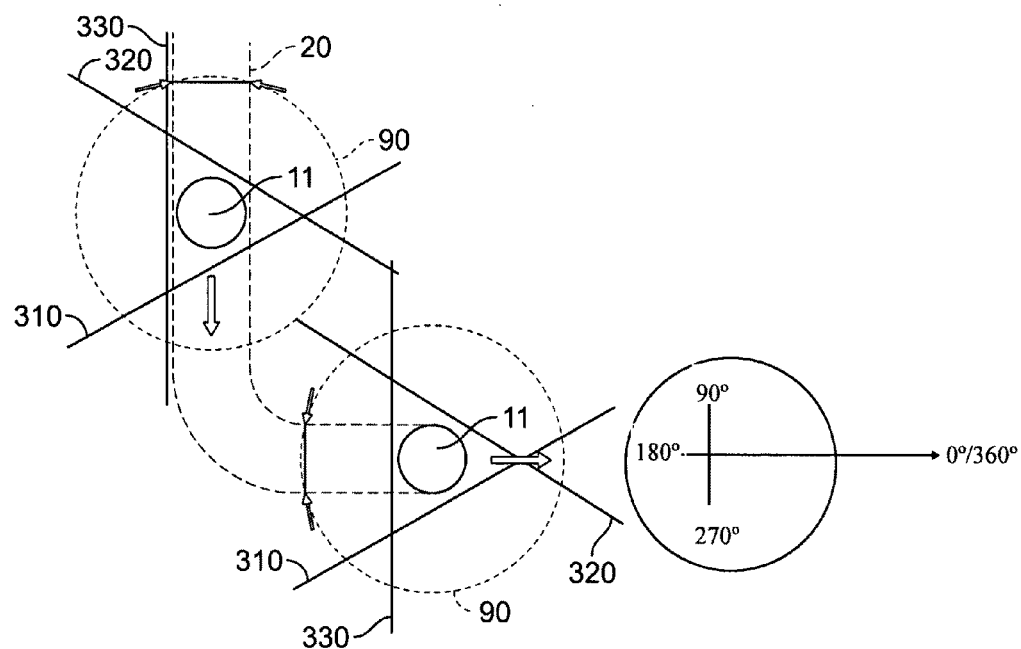
FIG. 9 illustrates a schematic view of a curved progression of the adhesive line and monitoring by the circular caliper according to an embodiment of the invention.

FIG. 9 shows a track-like progression whereby the adhesive line in the first position progresses from top to bottom and then progresses towards the right (e.g., as shown schematically by the second position in FIG. 9). For reasons of clarity of presentation, FIG. 9 does not show the entire rectangle 31, 32, and 33 of the individual cameras. But FIG. 9 shows the straight lines 310, 320, and 330 that are arranged around the application facility 11 such as to be fixed in position, because the cameras are also arranged around the application facility such as to be fixed in position. As a result, the position of the straight lines 310, 320, and 330 does not change upon track-shaped progression of the adhesive line with respect to the application facility 11. Arranged on the circular caliper 90 as indicated by the small arrows (shown in FIG. 9), the edges of the adhesive line 20 to be monitored are made to migrate from one image strip to another image strip on the circular caliper 90.

FIG. 9 shows in the [upper position] the adhesive line 20 is on image strip 32 on the caliper 90 as is indicated by straight line 320 The left edge of the adhesive line 20 is in the first position near the straight line 330, whereby only the camera assigned to image strip 32 is active.

If the adhesive line 20 progresses track-shaped, downwards, and towards the right the left edge of the adhesive line is first to migrate into the monitoring area between the straight line 330 and the straight line 320 such that, aside from the camera of image strip 32, the camera of image strip 33 also becomes active on the circular caliper 90.

FIG. 9 shows in the second, lower position of both edges of the adhesive line ck are at the end of the track-shaped progression in image strip 33 that is indicated by the straight lines 330. Consequently, only the camera assigned to image strip 330 is still active. Considering the overall progression, a global coordinate system results for the monitoring of the adhesive line 20 due to the circular caliper 90 being arranged around the application facility 11. The global coordinate system is arranged to be constant with regard to the application facility 11. Consequently, the software for assessment of the adhesive line 20 must take into consideration only the progression on the circular caliper 90.

According to an embodiment that is not shown, the circular caliper can also be provided by a surrounding track and/or orbit in essentially an elliptical, a polygonal form or as continuous lines, for determining the adhesive line by means of a scanning gray scale value.

Therefore, a method for recognizing a structure to be applied onto a substrate, preferably an adhesive line, with at least two cameras, in particular three or more cameras, is described. The structure is applied onto the substrate by an application facility, and is monitored by the cameras such that at least one overlapping area of the cameras is directed at the applied structure. The applied structure, in particular the edges of the adhesive line, is determined on a surrounding track around the application facility, whereby the surrounding track is predefined such that the applied structure intersects the surrounding track after being applied onto the substrate.

What is claimed:

1. A method for recognizing a structure to be applied onto a substrate, the structure being at least one adhesive line, the method comprising:
    applying the structure onto the substrate by an application facility having a plurality of cameras; and
    monitoring the structure applied onto the substrate by the application facility utilizing the cameras, the cameras having at least one overlapping area directed at the applied structure; wherein the edges of the adhesive line of the applied structure are determined on a virtual surrounding track around the application facility, wherein each camera monitors a segment of the surrounding track, the track essentially in the form of a circular line forming a circular caliper and the applied structure virtually intersects the surrounding track after being applied onto the substrate, wherein angle values of the circular line range from 0° to 360° to form a global coordinate system, a segment of the circular line having adjacent overlapping areas assigned to the images of the individual cameras and further automatically switching from one camera to the next camera when the adhesive line progresses from the segment of the circular line of one camera via the overlapping area to the segment of the circular line of a different camera.

2. The method according to claim 1, wherein the surrounding track comprises a closed form around the application facility for determining the adhesive line, the adhesive line on the surrounding track is monitored by means of a projection.

3. The method according to claim 1, wherein the adhesive line on the surrounding track comprises a circular caliper.

4. The method according to claim 1, wherein the adhesive line on the surrounding track comprises at least one of an elliptical form, a circular form, a polygonal form, and a plurality of continuous lines.

5. The method according to claim 1, wherein a center point of the surrounding track coincides with a site that corresponds to a site projected on the substrate by the application facility with regard to the adhesive line.

6. The method according to claim 1, wherein the cameras comprise at least three cameras to monitor the applied structure around the application facility on the surrounding track, wherein each camera utilizes one overlapping area to the neighboring camera.

7. The method according to claim 6, wherein each camera monitors a part of the surrounding track such that the camera image monitoring the individual parts of the surrounding track that are joined with the corresponding overlapping areas monitored by each camera to form a continuous surrounding track that progresses on the substrate and around the application facility.

8. The method according to claim 1, wherein a first camera covers at least a range of angles from about −10° to 130°, a second camera at least a range of angles from about 110° to 250°, and a third camera at least a range of angles from about 230° to 10°.

9. The method according to claim 1, wherein a strip of the camera image is processed by each camera comprising a sequence of images from the individual strips of the camera images wherein the closed surrounding track is assembled from the strips of the individual camera images.

10. The method according to claim 1, wherein the individual cameras are calibrated in order to assign an angle assignment, wherein a circular arc or circular line of the calibrating facility having marker points at 0°, 120°, and 240° for three cameras is used.

11. An apparatus for recognizing a structure to be applied onto a substrate, the structure is at least one adhesive line, comprising:
    at least one illumination module; and
    one sensor unit having only three cameras with at least one overlapping area, the cameras are configured around a facility for applying the structure such that each camera is directed at the facility for applying the structure, and wherein the edges of the adhesive line of the applied structure are determined on a virtual surrounding track around the application facility, and wherein the surrounding track is predefined such that the applied structure virtually intersects the surrounding track after being applied onto the substrate, wherein the three cameras are configured to monitor the applied structure around the application facility on the virtual surrounding track, wherein each camera utilizes one overlapping area to the neighboring camera.

12. The apparatus according to claim 11, wherein an axial longitudinal axis of the individual cameras approximately intersects, in the direction of view, an axial longitudinal axis of the application facility.

13. The apparatus according to claim 11, wherein at least three cameras are utilized, the cameras are arranged at equal distances from each other in a direction of the circumference.

14. The apparatus according to claim 11, wherein the individual cameras are configured such that images of all the cameras are stored in a sequence of images.

15. The apparatus according to claim 14, wherein each camera records a strip of the images to form a part of a sequence of images.

16. The apparatus according to claim 11, wherein the cameras forming the surrounding track approximately comprise a circular caliper.

17. The apparatus according to claim 16, wherein a center of the circular caliper approximately coincides with a site that corresponds to the longitudinal axis of the application facility on the substrate.

18. The apparatus according to claim 11, wherein each camera monitors a part of the surrounding track such that the individual parts of the surrounding track monitored by each camera is joined with the corresponding overlapping areas monitored by each camera to form a continuous surrounding track that progresses on the substrate around the application facility as a monitoring area.

19. The apparatus according to claim 11, wherein each individual camera comprises an overlapping area relative to the next camera of at least one of a 10° overlapping area and a 30° to 90° overlapping area.

20. The apparatus according to claim 11, further comprising a calibrating device, the calibrating device comprising individual form elements utilized for calibrating the individual cameras far the assignment of the angle assignment, wherein the individual form elements comprise an angle distance of approximately 10°.

21. The apparatus according to claim 20, wherein the calibrating device comprises at least three marker sites that are configured to be arranged in a circular arc of the calibrating device approximately at 0°, 120°, and 240° to calibrate the three cameras.

22. The apparatus according to claim 21, wherein the marker sites extend in an angle range of approximately 10°, and the marker sites comprise at least two form elements.

23. The apparatus according to claim 11, wherein only three cameras are utilized, the cameras are arranged at equal distances from each other in a direction of the circumference.

* * * * *